(12) United States Patent
Strom et al.

(10) Patent No.: US 8,197,403 B2
(45) Date of Patent: *Jun. 12, 2012

(54) OTOSCOPIC INSTRUMENT HAVING TIP ATTACHMENT AND EJECTING MECHANISM

(75) Inventors: John R. Strom, Moravia, NY (US); Cynthia A. Kuiper, Syracuse, NY (US); Chris R. Roberts, Skaneateles, NY (US); Michael E. Bausch, Livonia, NY (US); Allan I. Krauter, Skaneateles, NY (US); Eric M. Andreassen, Liverpool, NY (US); David C. Woods, Memphis, NY (US)

(73) Assignee: Welch Allyn, Inc., Skaneateles Falls, NY (US)

(*) Notice: Subject to any disclaimer, the term of this patent is extended or adjusted under 35 U.S.C. 154(b) by 1116 days.

This patent is subject to a terminal disclaimer.

(21) Appl. No.: 12/031,188

(22) Filed: Feb. 14, 2008

(65) Prior Publication Data

US 2008/0139888 A1 Jun. 12, 2008

Related U.S. Application Data

(62) Division of application No. 10/897,455, filed on Jul. 23, 2004, now Pat. No. 7,354,399.

(60) Provisional application No. 60/490,566, filed on Jul. 28, 2003, provisional application No. 60/507,473, filed on Sep. 30, 2003, provisional application No. 60/543,858, filed on Feb. 11, 2004.

(51) Int. Cl.
*A61B 1/267* (2006.01)

(52) U.S. Cl. .................................... 600/200; 600/193

(58) Field of Classification Search .............. 600/184, 600/193, 197, 213, 127, 129, 190, 208, 102, 600/105, 136, 137, 199–201; 277/636–637; 215/222, 223, 241, 295, 332; 220/293, 727; 359/828; 362/651; 374/158; 396/531; 439/102, 439/108, 286, 311, 314, 316, 318, 332, 337, 439/546, 616, 644, 649, 671–673, 740; 604/206, 604/533–535, 538, 539
See application file for complete search history.

(56) References Cited

U.S. PATENT DOCUMENTS 3,698,387 A 10/1972 Moore et al.
(Continued)

FOREIGN PATENT DOCUMENTS

WO WO99/42760 8/1999
(Continued)

OTHER PUBLICATIONS

European Search Report for EP Application No. 08798437.3; mailed Oct. 27, 2010, 7 pages.

(Continued)

*Primary Examiner* — Matthew J Kasztejna
*Assistant Examiner* — Ryan Henderson

(57) ABSTRACT

An otoscopic instrument includes an instrument head attached to a handle and a speculum tip actuator mechanism for receiving, retaining and selectively ejecting an otoscopic speculum tip element. The tip actuator mechanism includes an actuator knob rotatably attached to the instrument head in which the instrument head includes annular securement slots sized for receiving external engagement features of a speculum tip element which are rotatably fitted into the slot(s). The actuator knob further includes a pin for displacing a secured speculum tip element from the securing slot upon rotation in a predetermined direction in order to eject the tip element.

7 Claims, 13 Drawing Sheets

U.S. PATENT DOCUMENTS

| | | | |
|---|---|---|---|
| 3,815,584 A * | 6/1974 | Fiore | 600/184 |
| 3,840,004 A | 10/1974 | Heine | |
| 4,366,811 A | 1/1983 | Riester | |
| 4,454,370 A * | 6/1984 | Voznick | 136/221 |
| 4,488,701 A * | 12/1984 | Leigh-Monstevens | 248/637 |
| 4,567,924 A * | 2/1986 | Brown | 141/207 |
| 4,643,171 A * | 2/1987 | Riester | 600/200 |
| 4,662,360 A | 5/1987 | O'Hara et al. | |
| 4,702,537 A * | 10/1987 | Mattingly et al. | 439/152 |
| 4,785,796 A | 11/1988 | Mattson | |
| 4,997,419 A | 3/1991 | Lakatos et al. | |
| 5,363,839 A | 11/1994 | Lankford | |
| 5,390,663 A | 2/1995 | Schaefer | |
| 5,487,607 A * | 1/1996 | Makita et al. | 374/158 |
| 5,624,453 A | 4/1997 | Ahmed | |
| 5,720,756 A | 2/1998 | Green et al. | |
| 5,765,610 A * | 6/1998 | Brown | 141/383 |
| 5,795,067 A | 8/1998 | Fraden et al. | |
| 5,842,971 A | 12/1998 | Yoon | |
| 6,053,875 A | 4/2000 | Rosenbaum et al. | |
| 6,099,537 A | 8/2000 | Sugai et al. | |
| 6,106,457 A | 8/2000 | Perkins et al. | |
| 6,129,661 A | 10/2000 | Iafrati et al. | |
| 6,142,934 A | 11/2000 | Lagerway et al. | |
| 6,186,959 B1 * | 2/2001 | Canfield et al. | 600/559 |
| 6,190,310 B1 | 2/2001 | Cook | |
| 6,213,938 B1 | 4/2001 | Cook | |
| 6,254,271 B1 | 7/2001 | Lin | |
| 6,367,973 B2 * | 4/2002 | Yamaka | 374/158 |
| 6,383,133 B1 | 5/2002 | Jones | |
| 6,450,970 B1 | 9/2002 | Mahler et al. | |
| 6,511,420 B1 | 1/2003 | Farrell et al. | |
| 6,554,765 B1 | 4/2003 | Yarush et al. | |
| 6,659,943 B2 * | 12/2003 | Watanabe et al. | 600/178 |
| 6,698,625 B2 * | 3/2004 | Ufheil et al. | 222/190 |
| 7,354,399 B2 * | 4/2008 | Strom et al. | 600/200 |
| 7,494,273 B2 * | 2/2009 | Huang et al. | 374/158 |
| 2001/0014112 A1 | 8/2001 | Yamaka | |
| 2002/0085616 A1 | 7/2002 | Yu | |
| 2002/0193665 A1 | 12/2002 | Jones | |
| 2003/0063386 A1 | 4/2003 | Slawson et al. | |
| 2005/0027169 A1 | 2/2005 | Slawson et al. | |
| 2005/0043588 A1 | 2/2005 | Tsai | |
| 2005/0121912 A1 * | 6/2005 | Benscoter et al. | 285/401 |
| 2006/0020176 A1 | 1/2006 | Berall | |
| 2006/0159155 A1 | 7/2006 | Lantz et al. | |

FOREIGN PATENT DOCUMENTS

WO     WO 02/056756 A2     7/2002

OTHER PUBLICATIONS

Written Opinion of the International Searching Authority and International Search Report, Mar. 10, 2009, 7 pages.

* cited by examiner

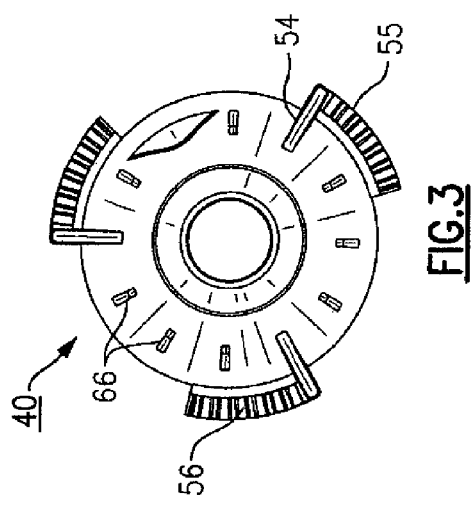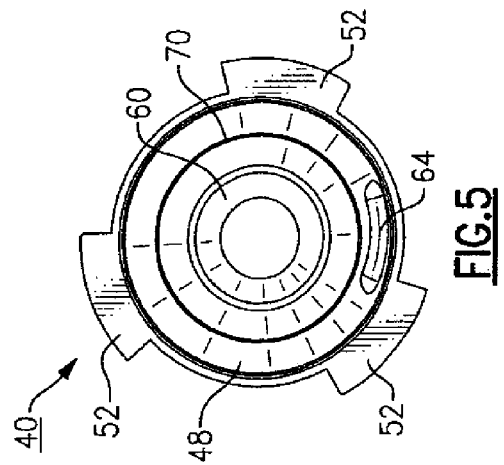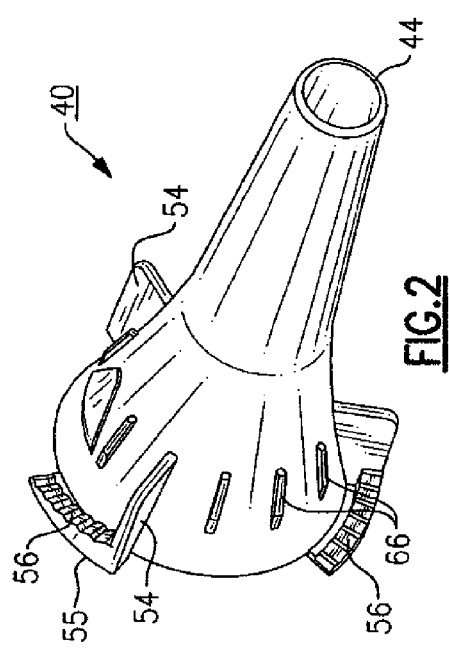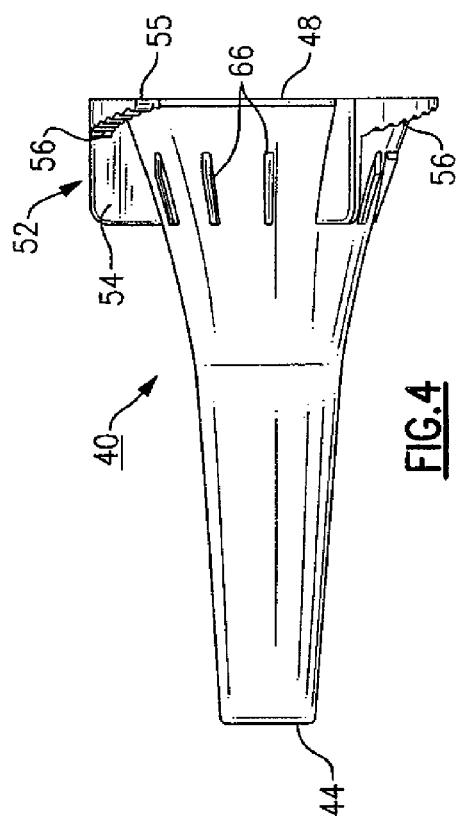

| | LENGTH OF TIP (FROM GAGE POINT I) | EAR CANAL INSERTION LENGTH | APERTURE SIZE | SLOPE | STACKING HEIGHT |
|---|---|---|---|---|---|
| 40' | .694 | .879 | Ø.156 (4.0mm) | 8" | .200 |
| 40 | .793 | .984 | Ø.167 (4.25mm) | 8" | .260 |
| 40A' | .694 | .897 | Ø.098 (2.5mm) | 14" | .156 |
| 40A | .793 | .984 | Ø1.08 (2.15mm) | 13" | .230 |

OTOSCOPIC INSTRUMENT HAVING TIP ATTACHMENT AND EJECTING MECHANISM

CROSS-REFERENCE TO RELATED APPLICATIONS

This patent is a divisional application of U.S. Ser. No. 10/897,455, filed Jul. 23, 2004 (U.S. Pat. No. 7,354,399), which claims priority under 35USC §119(e) based upon the following commonly owned provisional patent applications: U.S. Ser. No. 60/543,858, filed Feb. 11, 2004, U.S. Ser. No. 60/507,543, filed Sep. 30, 2003 and U.S. Ser. No. 60/490,566, filed Jul. 28, 2003, the entire contents of each being herein incorporated by reference.

FIELD OF THE INVENTION

This invention relates generally to the field of otoscopy and in particular to an improved otoscopic instrument and at least one improved releasably attachable tip element for use with otoscopic apparatus.

BACKGROUND OF THE INVENTION

Otoscopes are hand-held instruments that are commonly known in the medical diagnostic instrument field by practitioners and health care providers primarily for examining the ear, including the tympanic membrane, of a patient.

A typical otoscope is capable of being held in the hand of a practitioner and includes an instrument head having a distal frusto-conical insertion portion that permits overlying attachment of a disposable speculum tip. The disposable speculum tip is also preferably designed with a frusto-conical configuration to permit insertion to only an appropriate distance into the ear canal of the patient. Commonly, a ringlet of optical fibers encircles the tip opening of the insertion portion so as not impede with the user's visualization of the target, the fibers extending from a contained light source, such as a miniature incandescent lamp or bulb, that is housed within the instrument handle or a neck portion of the instrument head. The target (e.g., the tympanic membrane) is then viewed via a lens located in the proximal end of the instrument head, the lens being aligned optically with the distal tip opening of the insertion portion to permit user viewing. Often, the lens magnifies the view of the target.

Alternatively, a video camera or at least one solid state imaging element, such as a CCD- or CMOS-based imager, can be used to view the target in lieu of the lens, the image as processed being transmitted to a video monitor for display. In addition, the instrument head can include a receiving port for a pneumatic bulb, permitting insufflation (e.g., pneumatic otoscopy). These devices can also be used, in some instances, for examining the nose and throat in addition to the ear and ear canal, as well as to provide a general illumination and magnification system.

There are a number of perceived needs in the field currently. When considering the basic functions of the otoscope; e.g., visualization of the tympanic membrane, there have been expressed needs to increase the field of view and to provide greater magnification thereof, in addition to eye relief. Eye relief is practically defined as the distance between the most proximal optic of the instrument (e.g. the optic closest to the practitioner's eye) and the practitioner/user's eye when the full field is viewed. Magnification and eye relief are interrelated such that having an image overly magnified will bring the image "closer" to the eye of the practitioner, etc. Current otoscopes, due to the tortuous construction of the ear canal and the lenses that are used therein, cannot fit the entire tympanic membrane into the field of view.

To provide all of these noted improvements, in general, requires a tradeoff in depth of field, since optically all of the above factors are related. For example, the consequence of a depth of field loss is that for some patients with either long or short ear canals (as compared to a so-called "standard" or nominal ear canal), the tympanic membrane would no longer be in focus. This lack of focus is a distinct disadvantage and would seriously impact the practitioner's ability to give proper care.

There is yet another need generally in the field to be able to perform different diagnostic procedures as part of a comprehensive otoscopic examination. This need places increasing demands and constraints upon releasably attached disposable speculum tips used with the apparatus, in order to maintain cleanliness and prevent cross-contamination. A brief list of the requirements that are attributed to these type of otoscope tips include the following:

i) to achieve the "best view" (e.g., straighten the ear canal walls, maximize clear aperture);

ii) to effectively transmit light to the tympanic membrane and to collect light transmitted back from the tympanic membrane in order to effectively permit viewing thereof;

iii) to provide an effective substantially fluid-tight seal with the ear as well as with the instrument head in order to permit insufflation (e.g., pneumatic otoscopy);

iv) to allow placement and use of certain instrumentation while viewing through the optics, for cerumen (ear wax) removal.

v) to permit stacking of the tips in a compact fashion to facilitate storage in a dispenser or work kit;

vi) to be adequately cost-effective terms of manufacture in order to permit the tips to be disposable or replaceable;

vii) to prevent cross contamination;

viii) to fit a variety of patients (e.g., different sizes)

ix) to minimize the risk of unsafe insertion into the typical ear; and;

x) to fit relevant otoscopes used.

To meet this fairly comprehensive list of requirements, it becomes clear that any presently known otoscope tip would either optimize for only one or two of the above attributes, or perform moderately on a few of them. As a result, there are shortcomings, particularly with regard to disposable speculum tip designs that are presently available.

SUMMARY OF THE INVENTION

It is therefore one primary object of the present invention to provide an otoscopic apparatus that alleviates the above-noted problems and deficiencies of the prior art.

It is another primary object of the present invention to provide at least one or a family of otoscopic tips that provide optimum solutions for the above-noted requirements, with the fewest number of otoscope tips. This objective is especially important in that space in a physician/practitioner's office can be an issue, as well as the logistics and other issues that are often associated with managing various multiple tips.

Therefore and according to a first preferred aspect of the present invention, there is provided a tip element for securing to an otoscope, said tip element including a substantially axisymmetric body having a distal open end and a proximal open end, the tip element having at least one external engagement feature extending radially from the proximal end, the at least one external engagement feature being adapted for engaging a tip attachment mechanism of an otoscope. The at least one external engagement feature of the herein described tip element preferably is defined by a circumferential securing portion that is sized to fit within a securing slot of a tip attachment mechanism of an otoscope when the tip element is twisted thereupon in a first predetermined direction.

Preferably, the at least one external engagement feature further includes at least one axial portion depending from the circumferential securing portion, the at least one axial portion extending axially in a direction toward the distal open end of the tip element. In a preferred version, three (3) external engagement features, as described above, are provided, though this number can be suitably varied. A plurality of axial gripping ribs can also be provided on the exterior of the tip element, some or all of these ribs including the axial portions of the external engagement features.

According to another aspect of the invention, angled tabs, ribs or wedges are disposed about the periphery of the proximal end of the tip. Preferably, at least one of the engagement features of the tip element and the otoscope include sawtooth like "steps" in order to provide tactile feedback for the user when attached to the instrument head and to improve the engagement and sealed connection therebetween.

The otoscopic tip element can further include at least one interior engagement feature as well, for permitting attachment of the otoscopic tip element to an attachment portion of another type of otoscope, thereby permitting the tip element to be used more or less universally or interchangeably with various types of tip attachment mechanisms as provided on different otoscopes. The interior surface of the tip element is preferably polished in order to improve light transmissibility and further includes an interior sealing feature, such as an annular sealing ring, that permits or aids in the sealing of the tip element relative to the otoscope for insufflation purposes.

According to still another preferred aspect of the present invention, there is provided a tip element for an otoscope, the tip element comprising a substantially axisymmetric body having an open distal end and an open proximal end, and means for adaptively engaging with an instrument head of an otoscope, wherein the adaptive engaging means permits interchangeable attachment of the tip element to at least two different tip attachment mechanisms.

The adaptive engaging means preferably includes first engaging means for engaging an otoscope with a first tip attachment mechanism and second engaging means for engaging an otoscope with a second tip attachment mechanism. According to one version thereof, the first engaging means includes at least one external engagement feature and the second engaging means includes at least one internal engagement feature.

The at least one external engagement feature is provided radially relative to the body of the tip element and includes at least one circumferential securing portion sized for engaging a securing slot formed on an attachment portion of the instrument head. The at least one interior engagement feature includes at least one protrusion sized for engaging a bayonet-like slot in an attachment portion of an instrument head.

Preferably, the securing slots and the circumferential securing portions are substantially wedge-shaped, wherein the tip element is twisted in a first predetermined direction in order to engage the at least one circumferential securing portion with the at least one securing slot of the instrument head. According to a preferred version, a set of teeth are provided on an engagement surface of at least one of the securing slot and circumferential securing portion.

A plurality of tip elements can be provided in which the tip elements can be color-coded based on the type of patient used (size of the tip) and/or intended use thereof.

The tip elements as described are preferably disposable and to that end are fabricated such that their geometry permits stacking. At least one axial portion, depending from the at least one circumferential securing portion, assists in the stackability of a plurality of tip elements as well as provides a gripping surface to aid in attaching and removing the tip from the otoscope. In addition and according to a preferred version, a plurality of axial ribs additionally provided on the exterior of the tip element further provide means for gripping, as needed.

According to yet another aspect of the invention, there is provided an otoscopic assembly including at least one otoscopic instrument having an instrument head that includes at least one tip attachment mechanism; and a releasably attachable tip element in which the tip element includes a substantially axisymmetric body having an open distal end and an open proximal end and means for adaptively engaging the tip element with the instrument head, wherein the adaptive engaging means permits interchangeable attachment of the tip element to at least two different tip attachment mechanisms.

The otoscopic instrument includes an optical system contained therein that when aligned with an attached tip element permits the entire tympanic membrane to be viewed without panning of the instrument.

Additionally, an instrumentation tip element can be attached to the otoscopic instrument in lieu of the tip element previously described, the instrumentation tip element having an open-framed structure that defines openings that permit the insertion of at least one surgical instrument, such as a curved curette. The structure of the instrumentation tip permits instrument insertion without significantly interfering with the viewing of a target by the user.

Alternatively, an elastomeric seal assembly is further provided according to another embodiment which permits a substantially fluid-tight seal to be formed when the assembly is attached onto the exterior of a tip element. In addition, the assembly is shaped to permit the assembly to be selectively moved along the length of the tip element to optimize the seal.

According to yet another preferred aspect of the present invention, there is provided an otoscopic instrument comprising an instrument head including a distal insertion portion, the distal insertion portion being sized for receiving a substantially axisymmetric tip element and a tip attachment mechanism disposed on the instrument head having attachment features for receiving an retaining a tip element, the tip attachment mechanism including rotatable actuable means for selectively ejecting a tip element from the instrument.

The tip attachment mechanism preferably includes at least one circumferentially disposed securing slot on a distal facing surface of the instrument head that is sized for receiving a corresponding securing portion of a tip element. The rotatable actuable means includes an actuator knob that includes at least one pin element for displacing the tip element from the securing slots upon rotation of the knob in a predetermined direction. The rotatable actuable means is preferably biased so as to return the pin element to a home position, the means further including at least one indicator to indicate the predetermined direction to the user.

According to yet another preferred aspect of the present invention, there is disclosed a method for manufacturing a substantially axisymmetric speculum tip element for an otoscopic apparatus, the method including the steps of: providing at least one external engagement feature on the tip element permitting the tip element to be releasably attachable to an otoscopic instrument via a first tip attachment mechanism, the at least one external engagement feature extending radially from the proximal end of the tip element and manufacturing the tip element by means of a molding process.

According to still another preferred aspect of the present invention, there is disclosed a tip element for securing to an otoscope, said tip element comprising an internally open proximal portion and an internally open distal portion, said internally open distal portion having a distal end and an inner surface symmetric about an axis, said inner surface having a diameter that increases monotonically with distance proximally from said distal end; an inner diameter of said distal end being greater than 2.6 mm; a diameter of said inner surface equal to 7.0 mm at a distance greater than 18 mm proximal from said distal end; and an increase less than 6.2 mm in the length of a stack of said tip elements produced by adding one said tip element to said stack of said tip elements.

One advantage of the present invention is that a practitioner can use the herein described instrument without additional training being required.

An additional advantage of the present invention is that the improved tip design permits fewer tip sizes to be used while permitting enhanced otological examinations to be conducted.

The addition, by permitting use of a universal tip with both multiple existing otoscopes as well as the herein described otoscopic instrument design allows the practitioner having both prior art otoscopes as well as with the herein described otoscope to not have to keep track of the tips being used and permits the doctor or other practitioner to retain both types of otoscopes.

The addition of external bayonet-like engagement features on the tip elements creates a "grip" area that enables users to place the tips onto the existing otoscope more securely than is otherwise presently achievable. In addition, the improved draft angle and polished interior improve the efficiency of light transmission both into and out from the tip element.

Yet another advantage of the present invention is the non-contact releasability of the tip element from the otoscope.

These and other objects, features and advantages will become readily apparent from the following Detailed Description which should be read in conjunction with the accompanying drawings.

BRIEF DESCRIPTION OF THE DRAWINGS

FIG. 2 is an isometric view of a disposable otoscopic tip element used in conjunction with the otoscope of FIG. 1;

FIG. 3 is a front view of the otoscopic tip element of FIG. 2;

FIG. 4 is a side view of the otoscopic tip element of FIGS. 2 and 3;

FIG. 5 is a rear view of the otoscopic tip element of FIGS. 2-5;

DETAILED DESCRIPTION

The following description relates to a preferred embodiment of an otoscope that is made in accordance with the present invention as well as to preferred embodiments of a disposable, releasably attachable otoscopic tip element design. However, from the description there are many variations and modifications that will become apparent to one of sufficient skill in the field that can be made in accordance with the following inventive aspects.

In addition, several terms such as "distal", "proximal", "top", "bottom", "front", "rear", clockwise", "counterclockwise", and others are used throughout the discussion in order to provide a convenient frame of reference with regard to the accompanying drawings. These terms, however, should not be necessarily be regarded as limiting, except where so specifically indicated.

Figure 1:
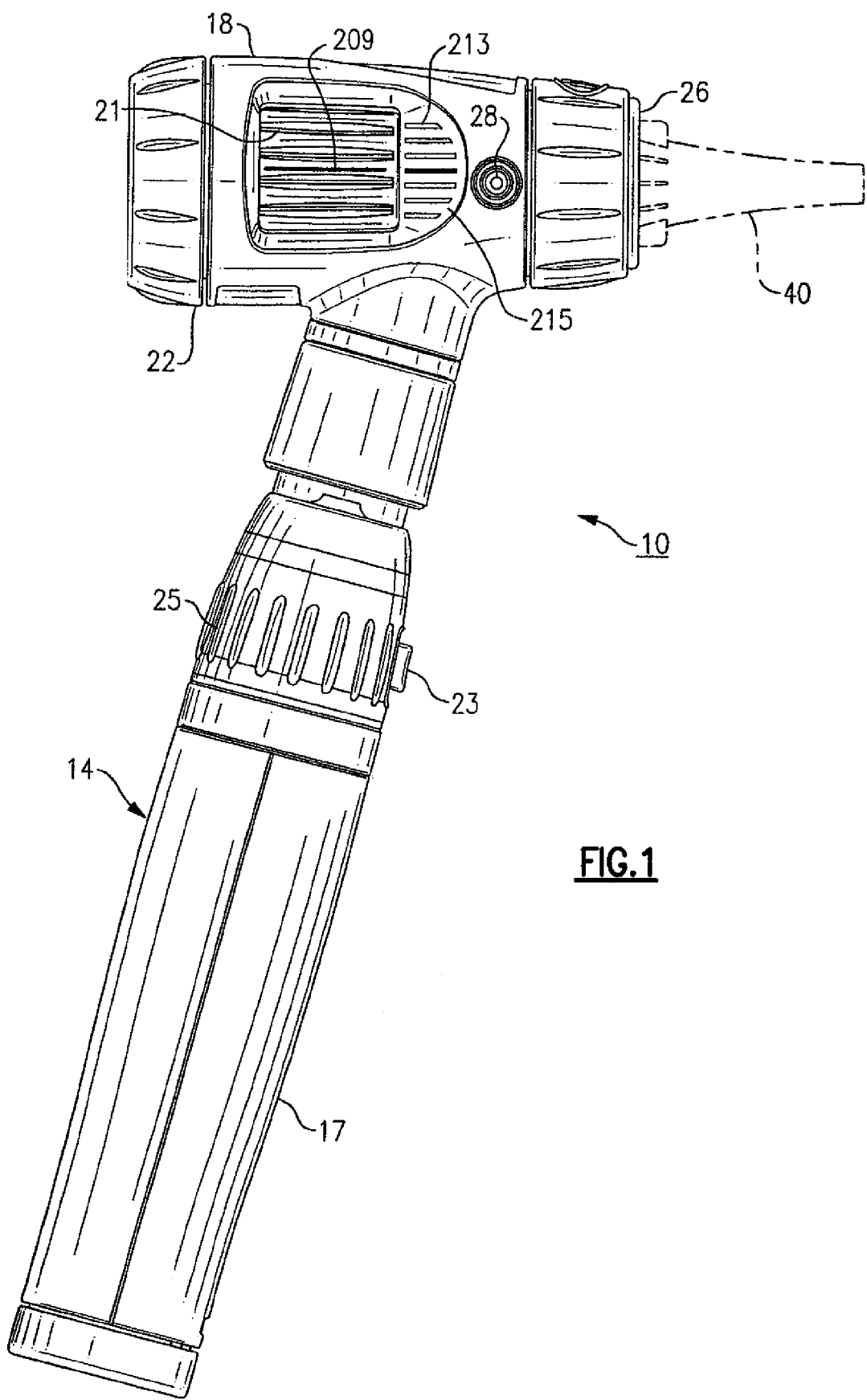
FIG. 1 is a side view of an otoscope made in accordance with the present invention.

Referring to FIG. 1, the otoscope herein labeled 10 includes a cylindrical handle portion 14 that contains a set of batteries (not shown) that are retained within an interior battery compartment (not shown), the handle portion having a bottom portion 17 that is preferably removable in order to permit the exchange of batteries. The handle portion 14 permits the instrument 10 to be hand-held and includes a top portion that is sized to accommodate an instrument head 18 which is fitted thereto. The instrument head 18 is substantially hollow so as to accommodate an insufflation port 28, the head being defined by a proximal end 22 and an opposing distal end 26 having an axisymmetric distal insertion portion 29, FIG. 6. The handle portion 14 further includes an actuable button 23, disposed above the bottom portion 17, that is used to power up the instrument as well as a rheostat 25 that is used to selectively adjust the illumination output of an illumination assembly that is contained in a necked or throat portion of the instrument head 18. It should be noted that each of the above features relating to the handle portion 14 are commonly known in the field and require no further explanation with regard to the present invention.

Before referring more specifically to a more detailed description of the remainder of the herein described otoscopic instrument 10, the following discussion refers to FIGS. 2-5 and more specifically to a preferred disposable speculum tip element 40 that is releasably mounted in overlaying relation onto the distal axisymmetric insertion portion 29 of the instrument 10. The tip element 40 is made preferably from a moldable plastic material, such as polypropylene, and is defined by a substantially axisymmetric configuration including a pair of open ends, namely a narrowed distal end 44 that tapers outwardly to a wider proximal end 48. The proximal end 22 also contains a number of non-axisymmetric features, discussed in greater detail below.

Figure 6:
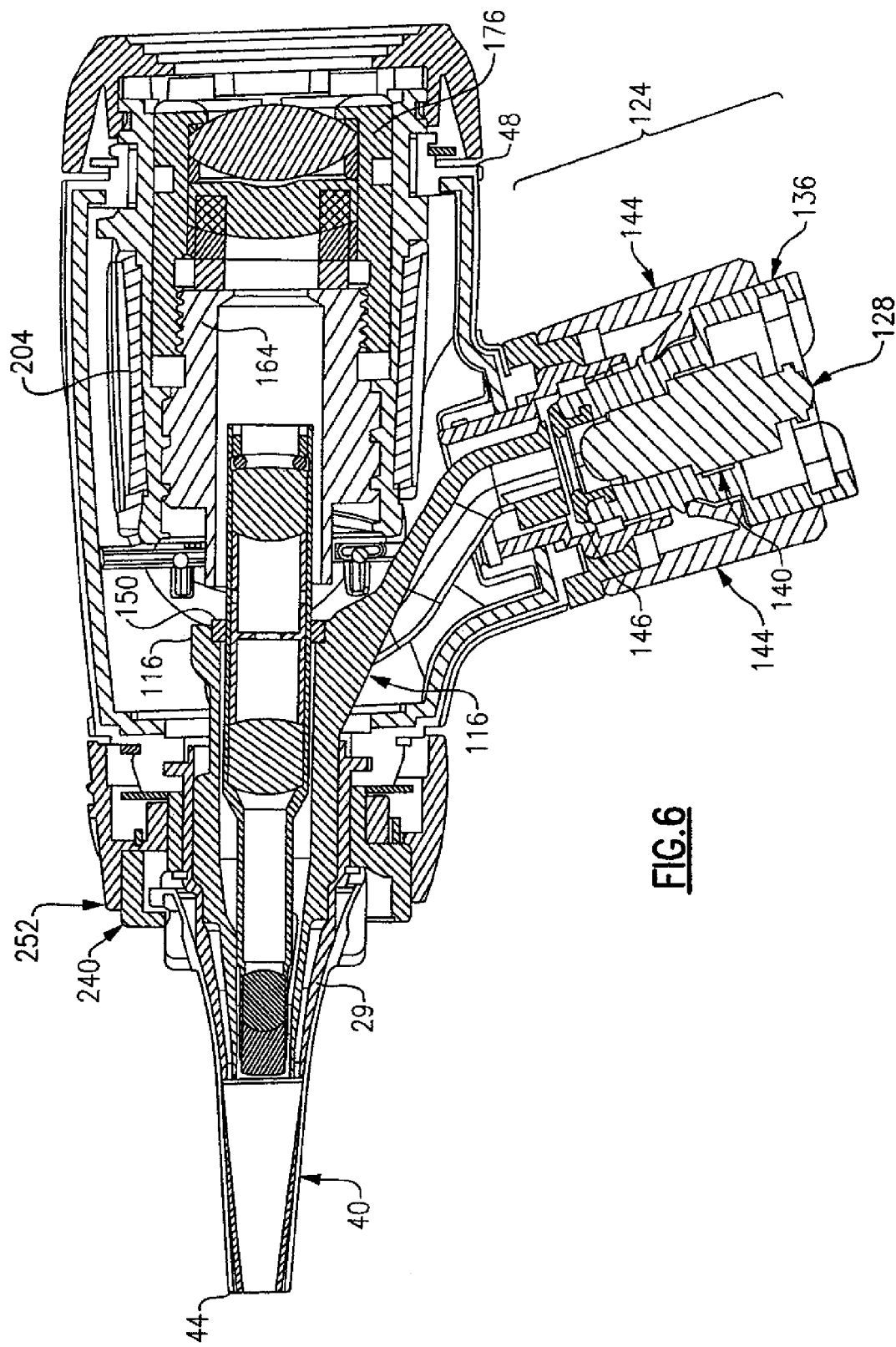
FIG. 6 is a side view, in section, of the instrument head of the otoscope of FIG. 1 as taken through lines 6-6 of FIG. 7.

For purposes of the following discussion, the tip element 40 shown in FIGS. 2-5 represents an "adult-sized" tip; that is, a tip element that is used for insertion into the ear of adult patients, though each tip element, regardless of the intended patient, commonly includes a number of engagement features, both external and internal, that permit the tip element 40 to be attached to the otoscope and more particularly to the distal axisymmetric insertion portion 29, FIG. 6. It will be readily understood that the tips can be made with varying sizes, depending on the patient.

In addition to the above, the present tip elements 40 each include a larger distal aperture and can comfortably extend a greater distance into the ear canal of a patient than any previously known disposable tip element of its aperture size.

Figure 15:
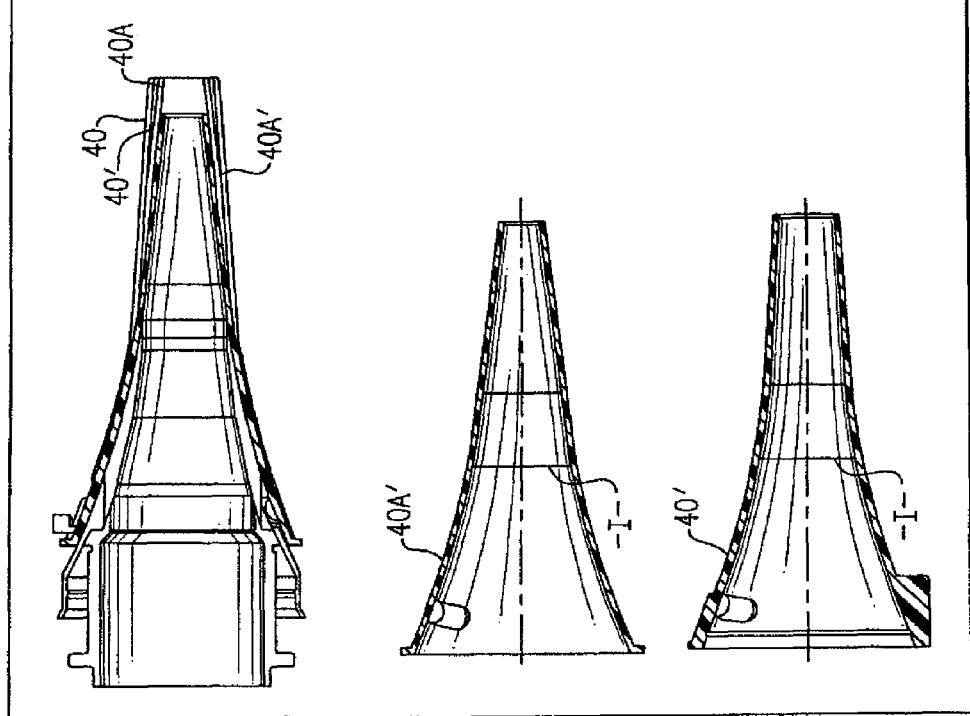
FIG. 15 is a side elevational view, partially in section, showing various design modifications to the otoscopic tip element as compared to certain known tip element designs.

Referring to FIG. 15, it has been determined empirically that a typical tip element has critical dimensions based on the anatomy of the ear canal and on the conical construction of the distal axisymmetric insertion portion 29 of the instrument 10. Increasing both the inner diameter of the distal end of the tip element 40 and the length of that portion of the tip element insertable into the ear permit a better access to and view of the tympanic membrane. To further illustrate this, a comparison between adult-sized tip elements 40 and pediatric (child) tip elements 40A made in accordance with present invention is provided with previously known tip elements 40', 40A' of the same types as herein represented in FIG. 15. Primarily, each tip element 40, 40', 40A, 40A' includes a pair of surfaces; a first surface represented from the proximal end of each tip element to an intermediate interface, indicated as -I-, needed to accommodate the cone of the distal axisymmetric insertion portion 29 of the otoscope; and a second conical surface-that extends from the intermediate interface -I- to the distal tip opening. The present tip elements 40, 40A are each substantially lengthened beyond the intermediate interface -I-, therefore permitting the tip element to be extended a greater distance into the ear canal of the patient. In addition, the distal tip aperture of each tip element 40, 40A is widened as compared with the depicted previous tip designs 40', 40A'. Each of the representative differences are represented tabularly in FIG. 15 along with an overlay of each of the tip elements 40, 40A, 40', 40A', as represented on each of an existing otoscope cone and an insertion portion that is made in accordance with the present invention.

Referring back to FIGS. 2-5, each tip element 40, regardless of the intended patient (e.g., pediatric, adult, etc.,), includes a plurality of external engagement features 52 that are located in relation to the proximal open end 48 of the tip element. According to this specific embodiment, three (3) such features 52, equally spaced from one another circumferentially by about 120 degrees, are provided, though the actual number of engagement features provided can easily be varied. Each of the external engagement features 52 according to this embodiment extends radially from the open proximal end 48 of the tip element 40 and commonly includes a circumferential securing portion 55 and a depending axial portion 54 forming a substantially L-shape, the circumferential securing portion 55 having a plurality of teeth 56 that are located on an engagement surface thereof. Additionally, the circumferential securing portion 55 is substantially wedge-shaped, the portion having a maximum thickness at the interface with the depending axial portion 54 and a tapered minimum thickness at an opposing end, thereby forming the ramped engagement surface. The depending axial portions 54 facilitate stacking of a plurality of tip elements 40, as well as provide a grip surface when attaching the tip elements to the otoscope. An additional plurality of spaced axial ribs 66 disposed between each of the depending axial portions, also provide a gripping surface when attaching the tip elements 40, as is described in greater detail in a later section.

The interior surface 60 of the herein described tip element 40 is polished to improve light transmissibility and further preferably includes an angled interior protrusion 64 that is located near the proximal tip opening 44. Referring to FIG. 5, the tip element 40 also includes an interior annular sealing ring 70, which is provided to assist in sealing the tip element to a conical portion of the distal axisymmetric insertion portion 29 of the instrument head 18, preferably for insufflating purposes.

Figure 7:
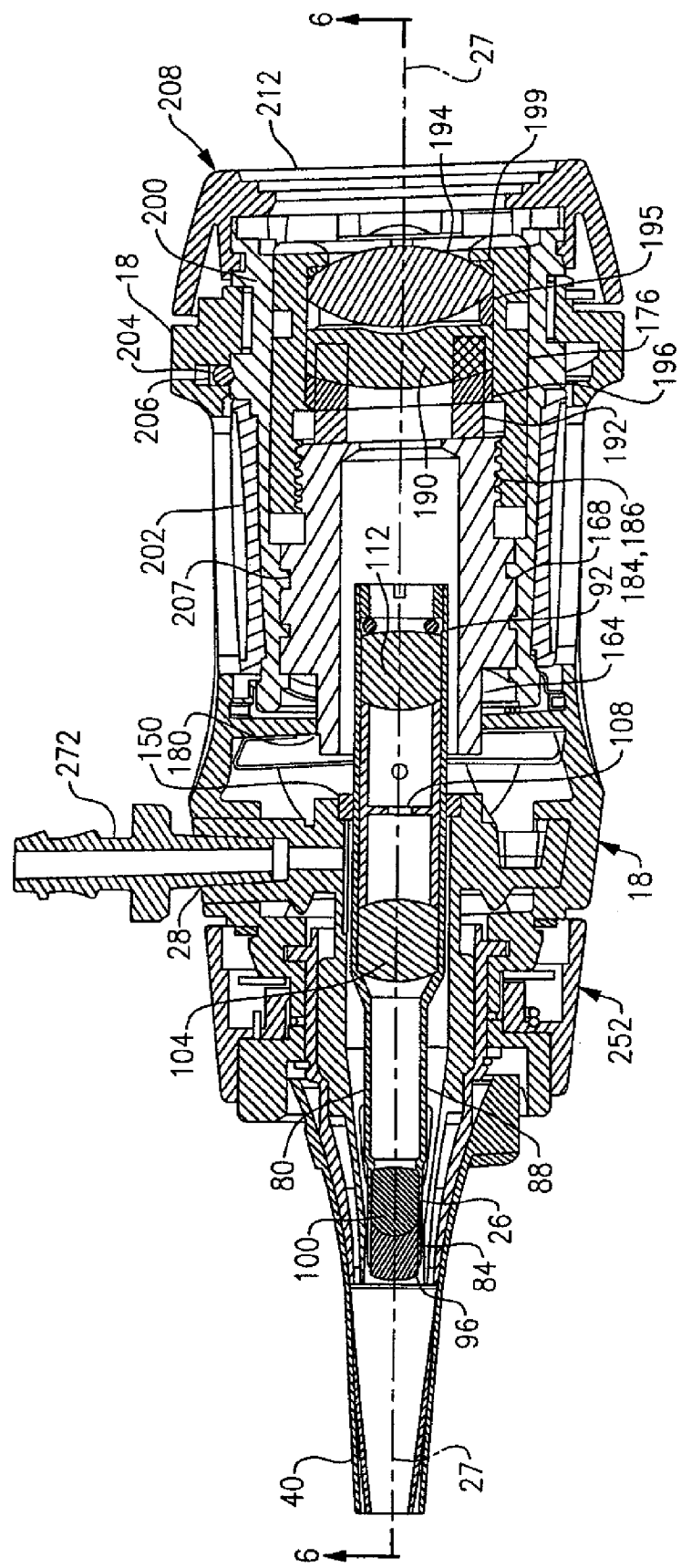
FIG. 7 is a top plan view, in section, of the instrument head of FIG. 6.

Referring now to FIGS. 6 and 7, the instrument head 18 retains a number of components, including the above-described disposable tip element 40 that is mounted in overlaying relation onto the distal axisymmetric insertion portion 29 and to an actuator mechanism, also described in greater detail in a later portion of this description that permits releasable attachment/disengagement of the tip element 40 to and from the instrument 10.

The above instrument 10 can be used for pneumatic otoscopy as is known through a hose connection 272, FIG. 7, partially shown, to the insufflation port 28, FIG. 7, the hose connection extending to a pneumatic supply (not shown) as is commonly known.

Within the confines of the instrument head 18, and beginning at the distal axisymmetric insertion portion 29 and extending proximally therefrom along a defined optical axis 27 is an imaging train that includes a predetermined number of optical elements, most of which are disposed within an open-ended tubular member 80. The tubular member 80 has a variable diameter that is defined herein by three axial sections, each axial section having a different interior diameter. The first axial section 84 of the tubular member 80 is defined by an initial diameter at the distal end thereof, and is sized for retaining an objective distal or front lens 96 and a lens 100, respectively, each of these lenses being disposed in adjacent relation to one another to form a doublet. The lenses 96 and 100 are mounted adjacently to one another, with the objective distal lens 96 partially extending outwardly from the distal most opening of the tubular member 80. The second axial section 88 of the tubular member 80 is defined, according to this embodiment, by a second interior diameter that is larger than the diameter of the first axial section 84, the second section linking an adjacent third section 92 that contains a first relay lens 104, an aperture stop 108, and a second relay lens 112, respectively, each of these elements being appropriately spaced from one another. The diameter of the third axial section 92 of the tubular member 80 is larger than either of the diameters of the first and second portions 84, 88 thereof. A functional discussion of the imaging train as well as that of the overall optical system of the herein described embodiment 10 is provided in a later portion herein.

Referring back to the overall assembly of the instrument 10, the tubular member 80 is retained within an inner former assembly 116 that is also positioned within the instrument head 18, wherein the first axial portion 84 of the tubular member 80 is sized to fit within the distal axisymmetric insertion portion 29. The inner former assembly 116 provides support for the tubular member 80 and further provides means for a plurality of extending optical fibers (not shown) from an illumination assembly 124. Referring to FIG. 6, the illumination assembly 124 is fitted within a necked or throat portion of the instrument head 18, the illumination assembly comprising a miniature incandescent lamp 128, the lamp being mounted within a base 136 and connected thereto via a lamp retainer 140, each of the above being held within a cylindrical sleeve member 144. A bumper guard 146 is placed onto the top of the lamp 128 in order to protect the lens envelope. The electrical connections of the illumination assembly with the batteries (not shown) provided in the handle portion 14, FIG. 1, as well as the interconnection to the rheostat 25, FIG. 1, are commonly known and do not form an essential part of this invention.

Preferably, the first axial portion 84 of the tubular member 80 is fitted within the interior of the distal axisymmetric insertion portion 29 such that the distal objective lens 96 is proximate the distal opening thereof, as shown in FIG. 6, the tubular member and surrounding inner former assembly 116 being placed through an opening in the instrument head interior that is sized for accommodating same. Preferably, the tubular member 80 is sealed to the proximal end of the inner former assembly 116 using a suitable adhesive, wherein a portion of the third axial section 92 of the tubular member extends therefrom. The seal, shown as 150 in FIG. 7, must be proximal (e.g., behind) the insufflation port 28 in order to permit insufflation to be achieved, such as through a hose connection 272, partially shown in FIG. 7, to a pneumatic supply. In other words, air entering the insufflation port 28 would flow forward (e.g., toward the insertion portion and the distal tip) meaning that the seal must be toward the proximal end beyond the insufflation port.

An eyepiece mechanism 160, as more specifically shown in FIGS. 6, 7, 13 and 14, is retained at the proximal end 48 of the instrument head 18, the mechanism including a substantially cylindrical lens carrier member 164 having a set of external threads 168 that are disposed adjacent to a square distal end 172 thereof. The square distal end 172 of the lens carrier member 164 is sized to be fitted into a corresponding opening 180, FIG. 7, provided within the interior of the instrument head 18 that retains the lens carrier member 164 and prevents the member from rotational movement. A tubular lens retainer member 176 is fixedly attached to the lens carrier member 164 by means of corresponding threaded portions 186, 184 on the interior distal end of the lens retainer member 176 and the exterior of the proximal end of the lens carrier member 164, respectively. The lens retainer member 176 includes an interior that is sized for receiving a pair of optical lenses 190, 194, that, when the lens retainer member and the lens carrier member are assembled to the instrument head 18, are aligned along the optical axis 27, FIG. 7, on which the optical elements 96, 100, 104, 112 of the imaging train are also aligned. The eyepiece mechanism 160 further includes a wave spring 192 and a lens retainer 196, each being disposed between the lens 190 and the lens carrier member 164. In addition, a spacer 195 is disposed between the lenses 194, 190 and an O-ring 199 is used to seal the lens 194 with the lens carrier member 176.

Figure 12:
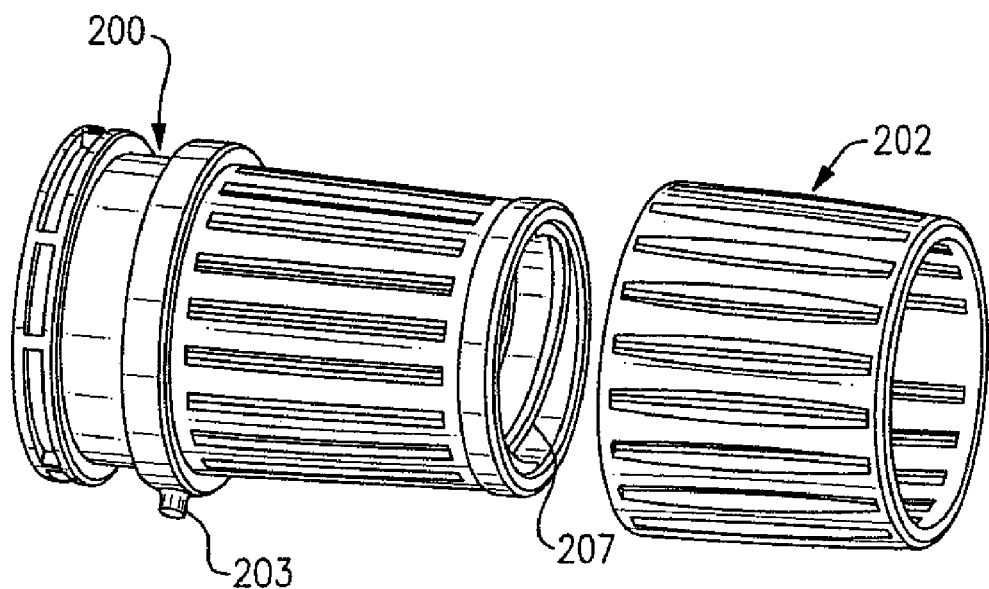
FIG. 12 is a partially exploded view of a focusing sleeve for use in the otoscope of FIGS. 1 and 6-9.
Figure 14:
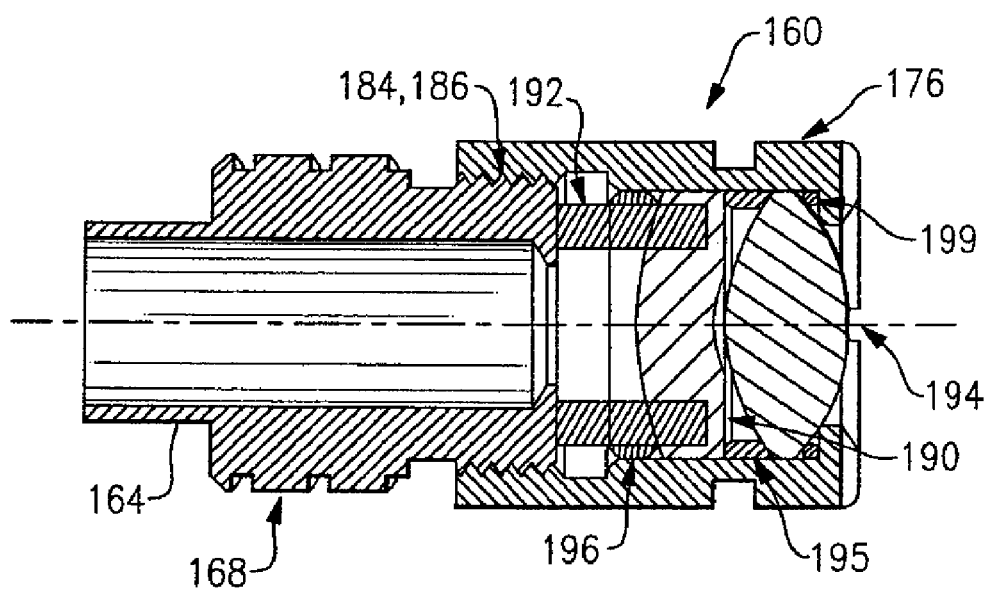
FIG. 14 is a sectioned view of the eyepiece mechanism of FIG. 13.
Figure 13:
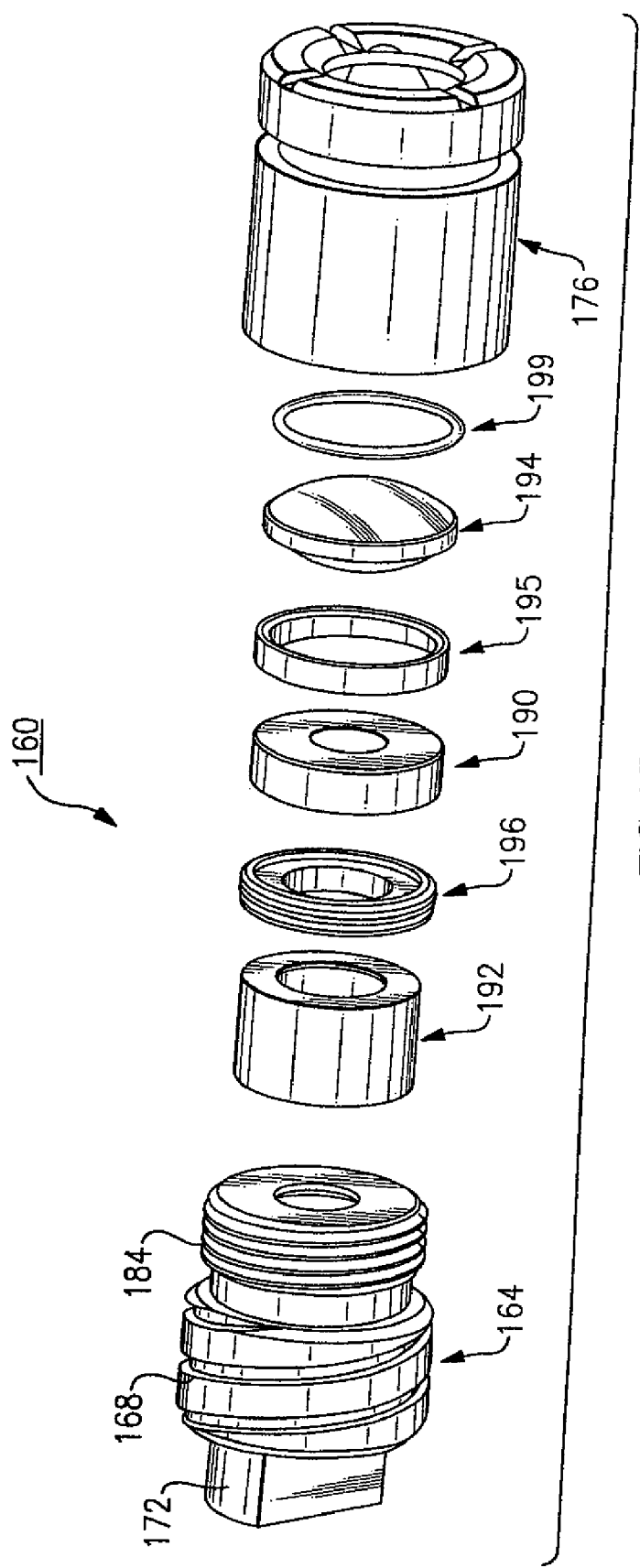
FIG. 13 is an exploded view of the eyepiece mechanism of the otoscope of FIGS. 1 and 6-9.

Referring to FIGS. 6, 7 and 12, the external threads 168 of the lens carrier member 164 engage with a set of corresponding threads 207 that are provided on the interior surface of a cylindrical focusing sleeve member 200 that is fitted thereupon in overlaying relation. The focusing sleeve member 200 has an axial length extending so as to project from the proximal end 48 of the instrument head 18 when the sleeve member is attached. A soft grippable elastomeric cover 202 overlays an axial portion of the sleeve member 200, the cover being mounted to rotate along with the sleeve member to an end of travel as determined by protrusion 203. A ball and compression spring 204, 206, shown only in FIG. 7, are each disposed within the interior of the instrument head 18, each being aligned with a single depression (not shown) that is formed on the exterior of the focusing sleeve member 200, the spring biasing the ball and forming a rotational detent that signals to the user that a predetermined factory-set focus position has been reached. A focusing knob 208 is snap fitted onto the extending proximal end of the focusing sleeve member 200. The focusing knob 208 includes a center opening 212, permitting the user/practitioner to view a target along the aligned optical axis 27, as does each of the focusing sleeve member 200 and the lens retainer member 176, respectively, and permitting selective axial adjustment of the eyepiece mechanism 160, FIG. 13, relative to the imaging train through rotational movement of the sleeve member 200. Preferably and during assembly, the lens retainer member 176 is adjusted relative to the lens carrier member 164. This adjustment permits creating a factory setting, for example, for humans at a certain focal length, and a different factory setting for example, for veterinary uses having a longer default focus position, wherein the sleeve member simply adjusts either above or below this position.

Figure 8:
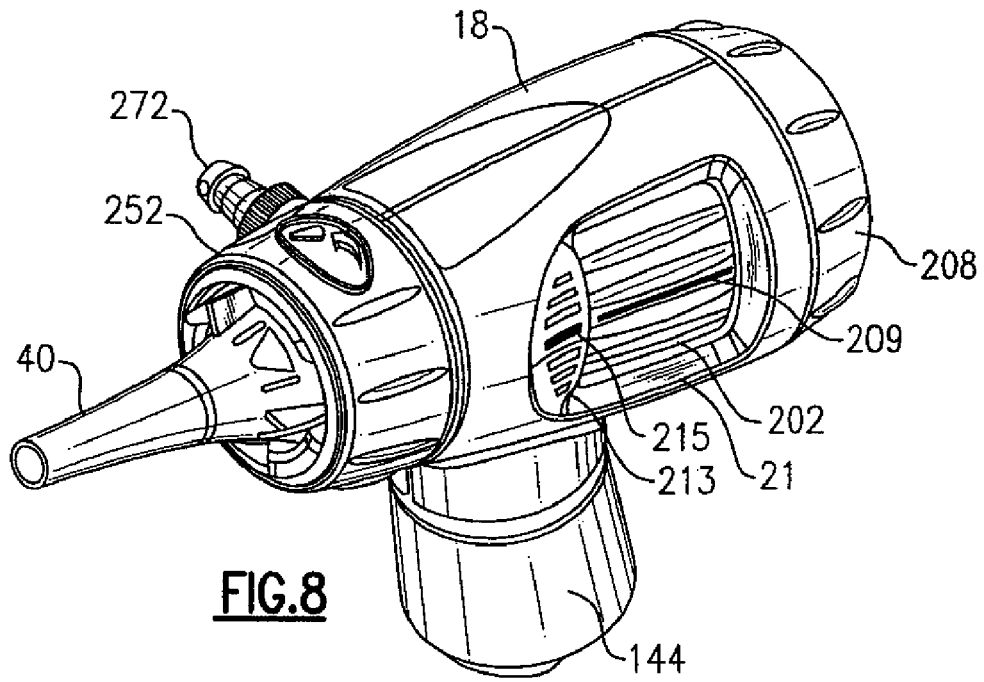
FIG. 8 is a front perspective view of the instrument head of FIGS. 6 and 7.
Figure 9:
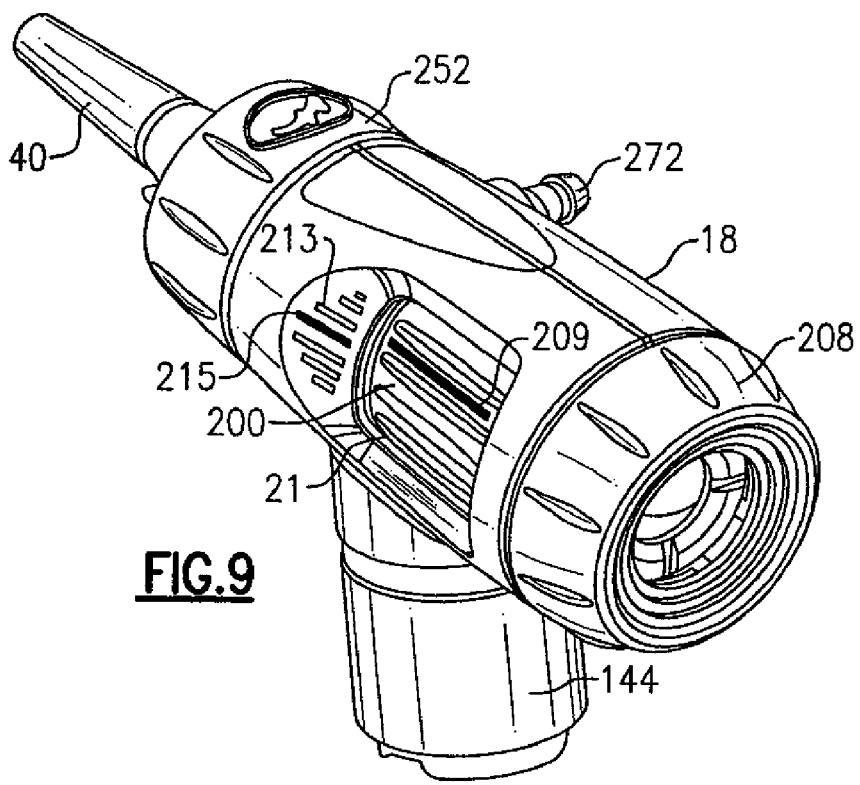
FIG. 9 is a rear perspective view of the instrument head of FIGS. 6-8.

For purposes of adjustability, the instrument head 18 further includes a pair of windows 21, FIGS. 8, 9, that are formed on opposing lateral sides thereof, wherein axial portions of the soft grippable elastomeric cover 202 to the sleeve member 200 are accessible to a user in addition to the focusing knob 208, as shown, for example, in FIGS. 8 and 9.

The tip actuator mechanism of the instrument 10 is now explained in greater detail with reference to FIGS. 2-5, 10, 11, and 18 (a)-(c). This mechanism includes a tip element retainer member 240 that is stationarily attached to the distal end of the instrument head 18, the retainer including a plurality of circumferentially spaced slots 242. In this embodiment, three slots 242 are provided, in which two of the slots include circumferential ramped surfaces 244. Each of the ramped surfaces 244 includes a set of teeth for engaging with the teeth 56 that are provided on the external engagement tabs 52 of the tip element 40. The tip actuator mechanism further includes a rotatable actuator knob 252 that is biased by means of a spring 256, the spring having an axial first end 260 that passes through a slot 264 in the actuator knob 252 to a hole 268 provided in the retainer member 240. The remaining end 269 of the spring 256 fitted within a slot 270 that is formed on the actuator knob 252. The retainer member 240 attaches to a front facing surface of the rotatable actuator knob 252, the actuator knob further including a pin 254, shown only in FIG. 18(c), that extends from the front facing surface into that slot 242 in the retainer member not having the circumferential ramping surfaces 244.

In operation, an otoscopic tip element 40 as described above, is attached onto the distal end of the instrument head 18 and more specifically in overlaying relation to the distal axisymmetric insertion portion 29, the circumferential securing portions 55 of each of the external engagement features 52 being fitted into the circumferential slots 242 that are provided in the tip element retainer member 240. The tip element 40 is then twisted, in this example, in a clockwise fashion, so as to engage the teeth 56 of two of the wedge-like engagement features 52 with the corresponding ramped surfaces 244 of the tip element retainer member 240, thereby providing positive engagement and providing tactile feedback to the user when attaching the tip element 40 to the instrument 10.

Figure 10:
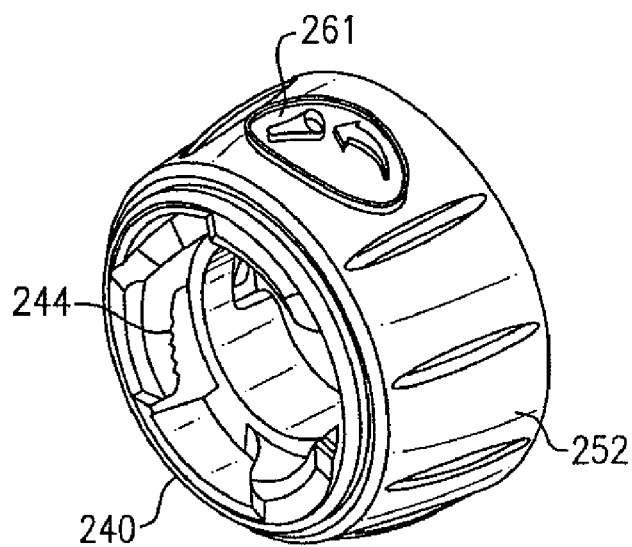
FIG. 10 is a partial front perspective view of the tip release actuator assembly of the otoscope.
Figure 11:
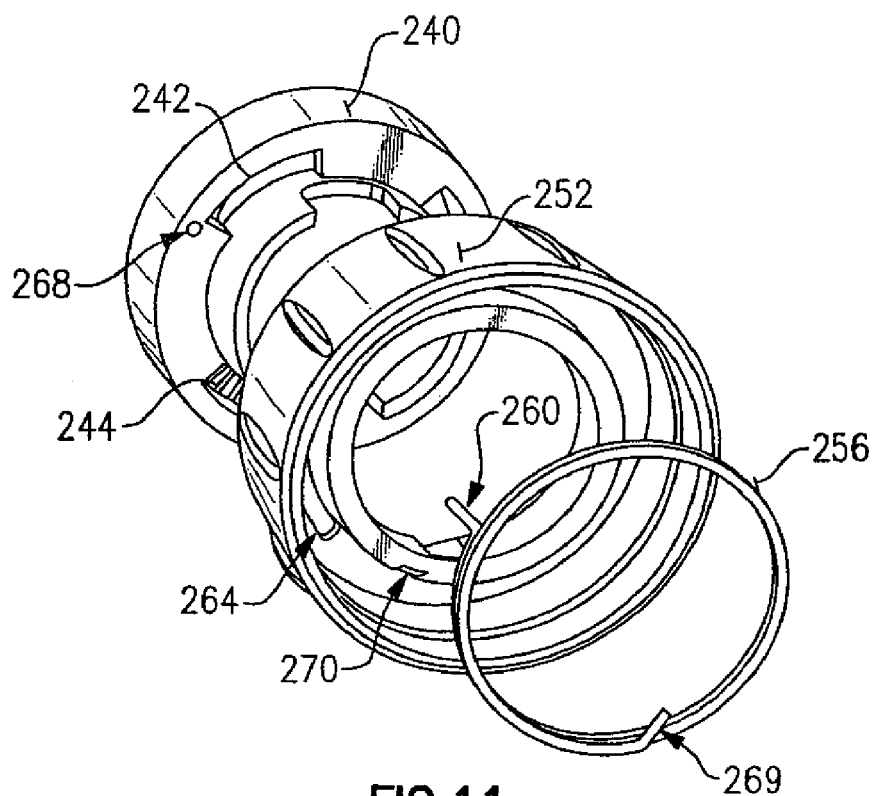
FIG. 11 is an exploded view of the tip release actuator assembly of FIG. 10.
Figure 18A:
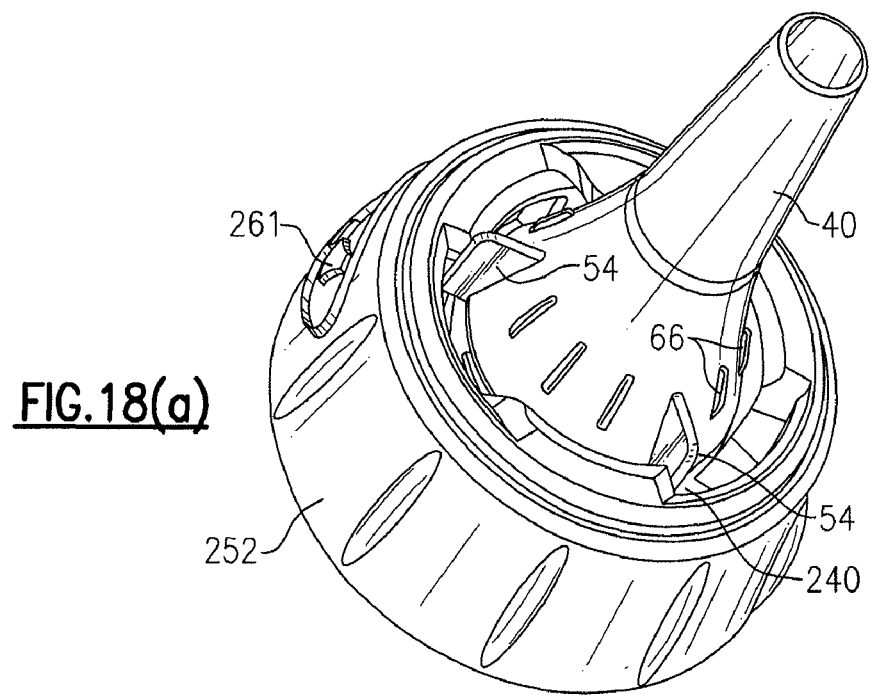
FIGS. 18(a) and 18(b) illustrate partial front perspective views of an otoscope tip ejection mechanism shown in two operative positions.
Figure 18B:
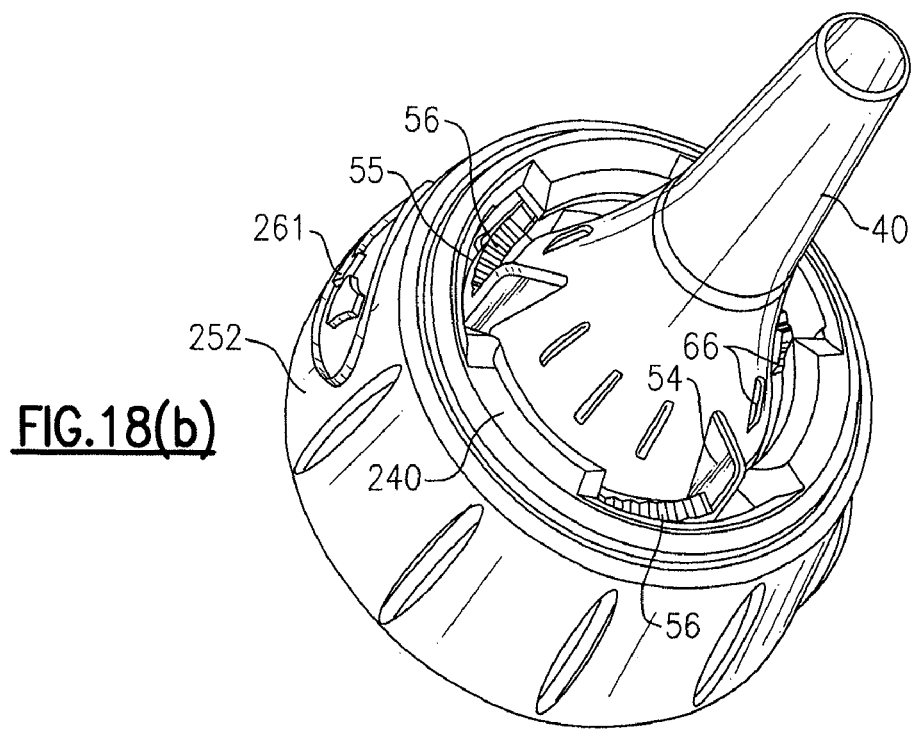
Figure 18C:
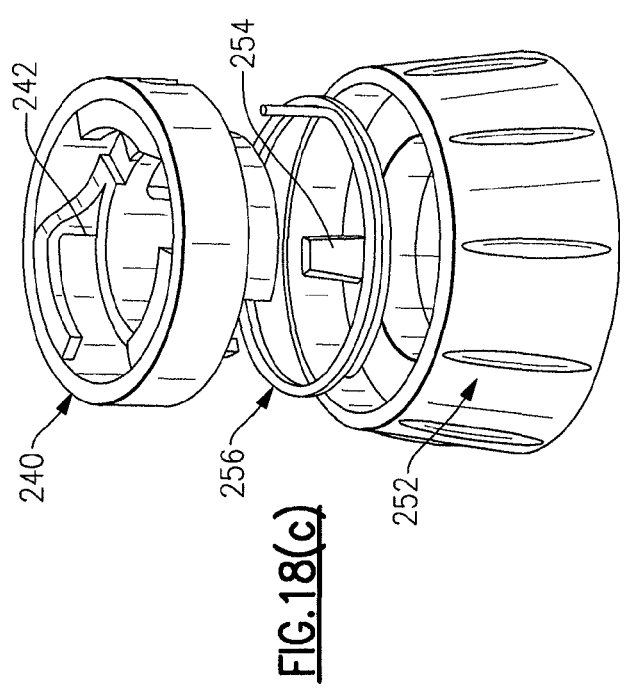
FIG. 18(c) is a partial exploded view of the otoscope tip ejection mechanism depicted in FIGS. 18(a) and 18(b)

Referring to FIGS. 10, 11 and 18 (a)-(c), and in order to release a tip element 40 from the instrument 10 following a patient examination, the actuator knob 252 is rotated in a counter-clockwise direction as denoted preferably by an indicator 261 located on the exterior of the actuator knob 252. This causes rotational movement of the knob 252 relative to the stationary tip element retainer member 240 and further causes the pin 254 to move into that slot 242 not having a ramped surface 244, driving the tip element 40 rotationally from the slots of the retainer member 240, releasing the tip element.

The design of the herein described tip element 40 is fairly universal; that is, the tip element is designed not only to fit the herein described instrument 10, but a number of already existing otoscopes, such as those employing bayonet-type attachment scheme as described by U.S. Pat. No. 3,698,387, and ejector-type mechanism as described be U.S. Pat. No. 4,366,811 the entire contents of each herein being incorporated by reference.

In operation, the use of the focusing mechanism permits relative movement of the optics of the eyepiece mechanism 160 relative to the imaging train of the instrument 10. The focusing sleeve member 200 and the soft grippable elastomeric cover piece 202 are each permitted to rotate about the optical axis 27, while the lens carrier member 164 and attached lens retainer member 176 are caused only to translate linearly due to the rotationally fixed connection with the instrument head 18. The remainder of the optical imaging train, disposed within the tubular member 80, including front objective lens 96 is stationary, and therefore relative movement is achieved, permitting focus adjustment to take place. As noted, the biased engagement of the ball by the compression spring into the depression of the focusing sleeve member 200 provides an indication of a predetermined fixed focus position (a preset position or distance between the eyepiece optics and the optics of the remainder of the stationary imaging train within tubular member 80) as sensed by the user/practitioner.

Indication of this preset or other focus position can be achieved by means of a visual indicator 209, provided on the exterior of the grippable elastomeric cover 202, portions of the cover being accessible through the windows 21 formed on lateral sides of the instrument head 18 to enable selective rotary movement of the focusing mechanism by mean of the soft grippable cover 202 in lieu of the focusing knob 208.

A scale of markers 213 are formed on edge portions of the instrument head adjacent the windows 21 including a preset focus position marker 215 that can be aligned with the visual indicator 209 which, in combination with the detent, further indicates the preferred nominal focusing position of the instrument 10.

In the predetermined fixed focus position, according to this embodiment, the overall length of the entire imaging system (e.g., the distance between the most distal and proximal optical surfaces including the eyepiece optics) is approximately 77.60 mm, the magnification is 1.63× when the tympanic membrane is located at a working distance of approximately 10 mm from the open distal end 44 of the speculum tip element 40, and the depth of field is approximately 3-5 mm. Additionally, the nominal eye relief is approximately 21.5 mm.

Figure 19:
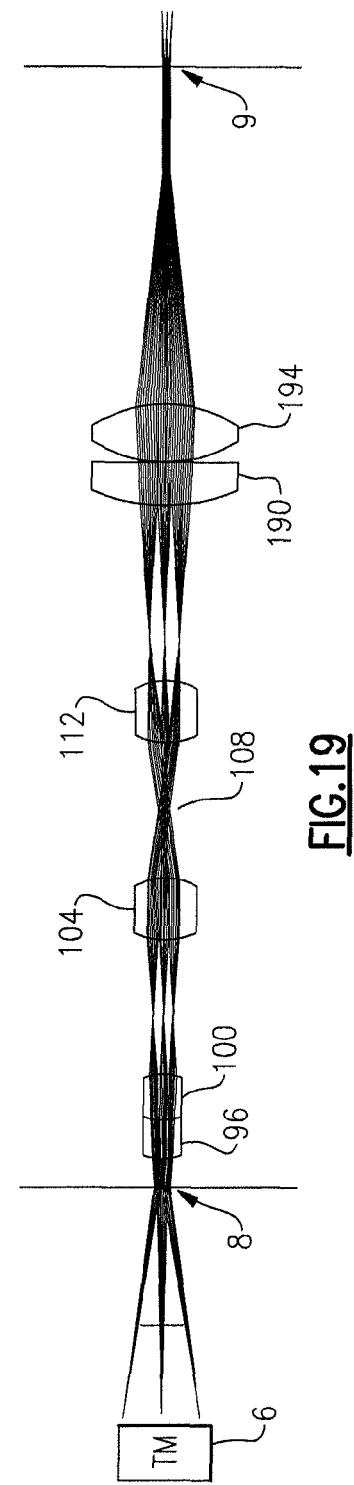
FIG. 19 is a ray trace diagram of the optical system of the otoscopic instrument in accordance with a preferred embodiment.

Referring to FIGS. 7 and 19, the aperture stop 108 is optically conjugate to both the entrance pupil 8 and the exit pupil 9 of the entire optical system. The axial location and the size of the entrance pupil 8 are critical in achieving an unobstructed view of the entire tympanic membrane, shown schematically in FIG. 19 as 6. If the entrance pupil 8, which is located distally relative to lens 96, is too close to that lens, there is excessive obstruction of rays emerging from the upper edge of the tympanic membrane 6 by the end of the tip element 40. If the entrance pupil is located too far distally from lens 96, then there is excessive obstruction of rays emerging from the upper edge of the tympanic membrane 6 by the edge of the first or last optical surface of the doublet consisting of lens 96 and lens 100. In this embodiment, the entrance pupil 8 is located in close proximity to the objective lens doublet (lenses 96 and 100), such as to achieve the optimal view of the tympanic membrane 6 with minimal ray obstruction. Similar considerations apply to the physical size of the aperture stop 108.

The exit pupil 9 is located approximately 21.5 mm proximal to the most proximal optical surface of lens 194. This distance provides: a) optimal image stability in relation to lateral movement of the user's eye during an ear examination; b) optimal viewing of the tympanic membrane 6 with minimal ray obstruction; and c) the ability to accommodate a large range of spectacle lenses. This exit pupil location relative to lenses 190 and 194 is constant regardless of the position of the focusing mechanism.

Figure 20:
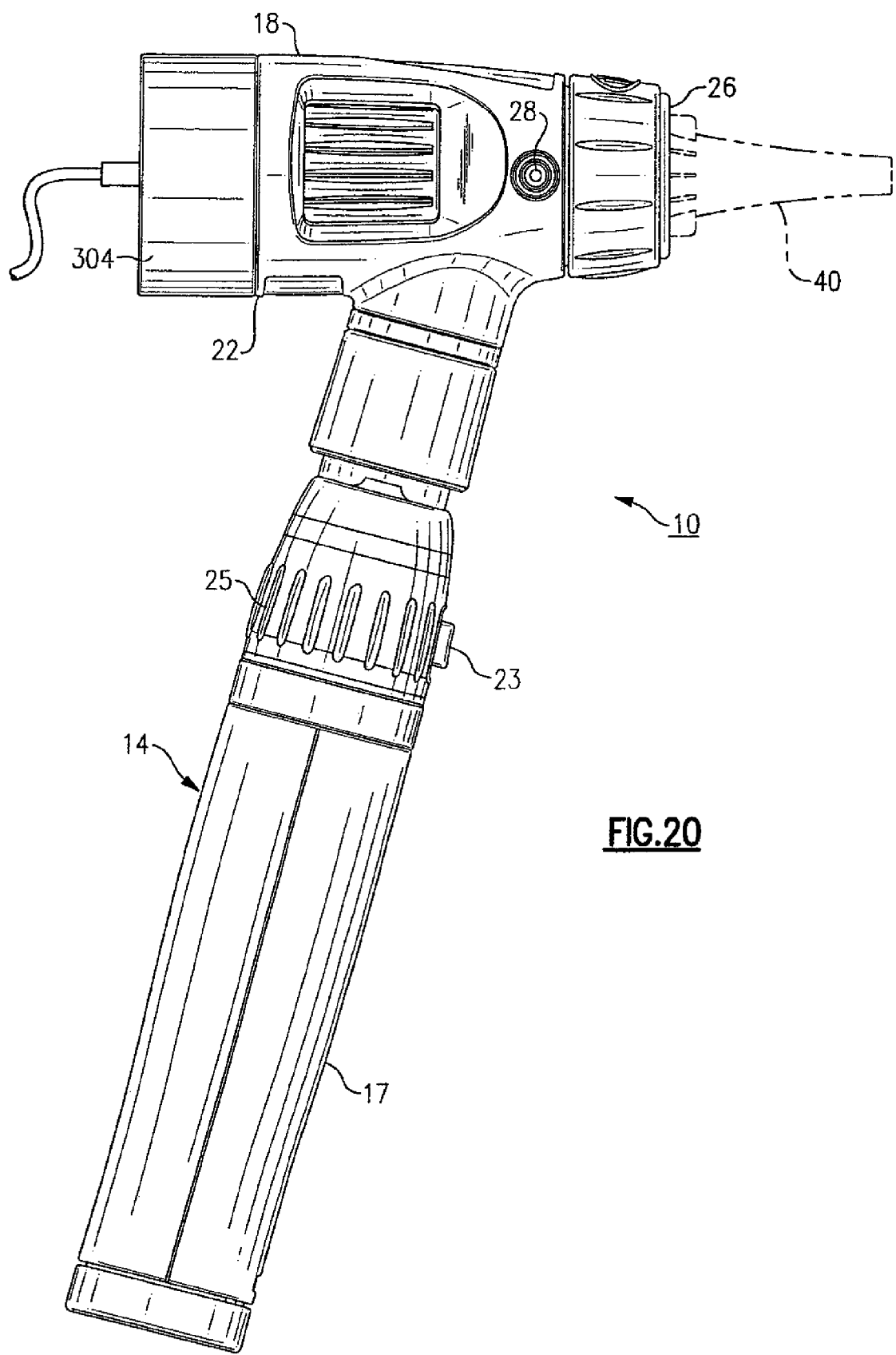
FIG. 20 is a side elevational view of the instrument head as attached to an electronic imager used as a viewing means in lieu of an eyepiece mechanism.

The optical system described herein can easily be expanded to video/imager human otoscopy by adding an electronic imager assembly 304 onto the proximal end of the otoscope, as shown in FIG. 20. In addition, the herein described instrument can similarly be used for optical or video/imager based veterinary otoscopy. Furthermore, one can easily and conveniently modify the optical system shown herein by using appropriate optical adapters, e.g., by adding optics to the viewing means shown in the preceding embodiment.

Selective focusing travel of the lenses 190 and 194 of the eyepiece mechanism is such as to give the user the ability to achieve a close-up view (important in infant ear examinations) and a distant view (important in throat and nasal examinations). The working distance between the tympanic membrane 6 and the first optical surface of the distal lens 96 is optimized according to this embodiment to fall around 27 mm; this latter dimension is clinically important because it provides the correct setup between inserting the otoscope too deeply into the ear canal. In addition, the herein described optical system produces an erect image of the tympanic membrane to the user at the viewing means.

The imaging train substantially places the objective doublet 96, 100 within the ear at the time of examination, since this optical element is located in the distalmost portion of the instrument head 18, and much closer to the tympanic membrane than any typical otoscope. As a result, a greater (e.g., wider) field of view is achieved, i.e., an area larger than that of the tympanic membrane can be viewed by the user in an operative position of the instrument. Moreover, the entrance pupil location enables an unobstructed view of a typical 7 mm adult tympanic membrane for working distances greater than or about 27 mm, wherein the working distance is defined as the spacing separating the tympanic membrane from the distal surface of the lens 96 or approximately, according to this embodiment, about 9.5 mm from the tympanic membrane to the distal end of the tip element 40. By creating a field of view greater than about 9 mm at a working distance of about 33 mm using the herein described optical system, the entire tympanic membrane can be observed without panning of the instrument 10. The separation between the optics contained within the tubular member 80 and the eyepiece optics 190, 194 is variable in order to permit focusing in a suitable range of working distances and compensating for user's accommodation. As a result of the foregoing, an appropriate tradeoff is achieved between magnification, field of view, working distance, eye relief and focusing range. The latter parameter is additionally critical so as to allow the instrument to be further used, for example, for examinations of the throat and/or nose of the patient.

An additional problem associated with otoscopes, particularly imaging styles with optics located in the main line of sight, is that inserting instruments into the ear is very difficult to do while seeing through the optics. Diagnostic otoscopes and others enable a magnifying window to slide to the side or out of the way, but the resulting view is typically extremely compromised and the use of a curette through the constrained area is far from ideal.

Figures 16, 17:
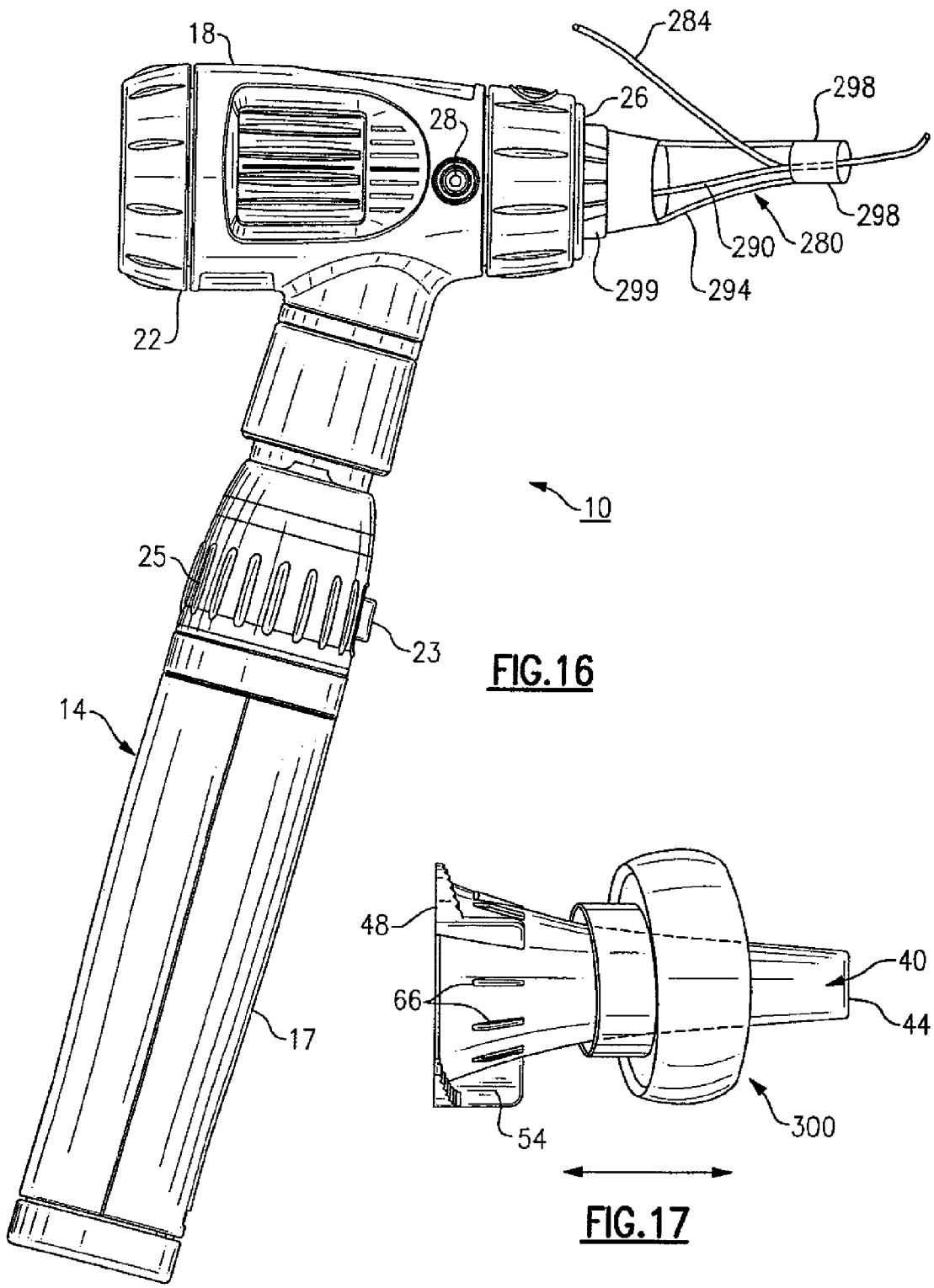
FIG. 16 is a side view of an instrumentation tip element made in accordance with one aspect of the present invention.
FIG. 17 depicts an elastomeric assembly which is attachable to the tip element of FIGS. 3-5.

Referring to FIG. 16, an instrumentation tip 280 and a curette 284 are herein described dealing with the above-stated problem, which allows for significantly better instrument insertion while still viewing through the optics of an otoscope 10, such as that previously described, for example. The instrumentation tip 280 according to this embodiment is essentially a cage-like member 290 that extends the tip contacting the patient away from the otoscope, leaving a large open area into which the curette 284 can be inserted and manipulated. It should be understood that the tip that contacts the patient can take a variety of shapes and sizes as can the cage distance and support structure. In this embodiment, the cage-like member 290 is defined by three legs 294 extending between a distal ear insertion portion 298 and a proximal otoscope attachment portion 299, the entirety of the cage-like member being approximately one inch in length. The curette 284 is ideally curved to maximize the ability to manipulate it within the defined open areas between the legs 294. Alternative configurations where some or the entire cage is reusable or integrally attached to the scope should be readily apparent to one of sufficient skill in the field. However, the advantage of a fully disposable version is that the nature of instrumentation implies that some foreign body has been removed from the ear which increases the exposure and risk of cross contamination. It should be noted that the length of the tip and the otoscope optics must be matched such that the area in front of the tip is in focus to the use of instrumentation. The otoscope attachment portion 299 preferably includes external engagement features, such as shown in FIGS. 2-5, and or including an internal bayonet, depending on the tip attachment mechanism of the otoscope used therewith.

Referring to FIG. 17, a further problem, with disposable otoscope tips is that they do not seal well to the majority of most patient's ears. Further, soft over-mold tip versions seal relatively well, but prevent insertion within the ear beyond the depth at which the elastomer interferes with the ear. Therefore, although the tips achieve an effective seal, they prevent or impede the visualization that is essential during insufflation. It serves no practical purpose to seal and insufflate if the tympanic membrane cannot be viewed during this process, as the movement (or lack thereof) creates the basis for diagnosis.

To deal with the above stated problem, an elastomeric seal accessory 300 is provided according to one embodiment that slides onto the exterior of a disposable tip element, such as those previously described in FIGS. 2-5, or other version having a substantially conical body. This elastomeric seal accessory 300 provides a good seal to the patient ear and is adjustable in its axial position on the tip 40. Therefore, the tip can be set for "deeper" insertion or shallow insertion so that both the seal as well as the proper insertion depth for visualization can be achieved. This seal accessory 300 is preferably compliant enough that it is set at the distal end of the tip and "pushes in" as the practitioner inserts the tip into the ear canal (not shown).

Additional features, such as markings on the tip and depth setting provide advantages. The geometry of the elastomeric seal accessory 300 itself also creates an advantage since it is mushroom shaped in the present embodiment, allowing the accessory to collapse in order to seal with a variety of ear canal sizes. An additional advantage exists in the case of the present mushroom-shaped design in that these tips are less sensitive to positional variation (i.e., the accessory can be sealed at many different positions along the tip). Therefore, the axial position of the accessory 300 can easily be varied along the length of the tip in order to effectively optimize the seal. It should be readily apparent that there are alternative geometries that could be conceived for the elastomeric seal accessory, embodying the inventive concepts employed herein.

PARTS LIST FOR FIGS. 1-20

6 tympanic membrane
8 entrance pupil
9 exit pupil
10 otoscope or instrument
14 cylindrical handle portion
17 bottom portion
18 instrument head
21 windows
22 proximal end
23 actuable button
25 rheostat
26 distal end
27 optical axis
28 insufflation port
29 distal axisymmetric insertion portion
40 adult speculum tip element
40A pediatric speculum tip element
40' adult/prior art speculum tip element
40A' pediatric/prior art speculum tip element
44 distal end, tip element
48 proximal end, tip element
52 external engagement features
54 depending axial portion
55 circumferential securing portion
56 teeth
60 interior surface, tip element
64 angled internal protrusion
66 gripping ribs
70 annular interior sealing ring
80 tubular member
84 first axial portion
88 second axial portion
92 third axial portion
96 distal lens
100 lens
104 first relay lens
108 aperture plate
112 second relay lens
116 inner former assembly
124 illumination assembly
128 lamp
136 base
140 lamp retainer
144 sleeve member
146 bumper guard
150 seal
160 eyepiece mechanism
164 lens carrier member
168 external threads 172 distal end
176 lens retainer member
180 opening
184 threaded portion
186 threaded portion
190 lens
192 wave spring
194 lens
195 spacer
196 lens retainer
199 O-ring
200 focusing sleeve member
202 grippable elastomeric cover
203 protrusion
204 ball
206 compression spring
207 internal threads
208 focusing knob
209 indicator, visual
212 center opening
213 markers, scale
215 preset focus position marker
240 tip element retainer member
242 slots
244 circumferential ramped surfaces
252 actuator knob
254 front face pin
256 spring
260 axial end
261 indicator
264 slot
268 hole
269 remaining end
270 slot
272 hose connection
280 instrumentation tip
284 curette
290 cage-like member
294 legs
298 distal ear insertion portion
299 proximal otoscope attachment portion
300 accessory, elastomeric seal
304 electronic imager assembly It should be readily apparent that other variations and modifications will be readily apparent to those of ordinary skill in the field. For example, the otoscopic instrument described herein could include tip attachment mechanisms for receiving either engagement feature of the herein described tip element. Other variations embodying the scope of the invention could easily be imagined, as defined in the following claims:

The invention claimed is:

1. An otoscopic instrument comprising:
an instrument head attached to a handle; and
a tip actuator mechanism for receiving, retaining and selectively ejecting an otoscopic speculum tip element from said instrument head, said tip actuator mechanism including an actuator knob rotatably attached to said instrument head, circumferentially disposed annular securing slots disposed on said instrument head, each annular securing slot sized for receiving a corresponding external engagement feature of said speculum tip element securable by rotation into said annular securing slot, said actuator knob having a pin for displacing said speculum tip element from said annular securing slots upon rotation in a predetermined direction from an initial position, thereby ejecting said speculum tip element.

2. An instrument as recited in claim 1, including three circumferentially equispaced securing slots.

3. An instrument as recited in claim 1, wherein said actuator knob is biased by a spring to return to said initial position upon release thereof.

4. An instrument as recited in claim 1, wherein said actuator knob includes at least one indicator thereupon to indicate the predetermined direction to a user.

5. An instrument as recited in claim 2, wherein two of said three securing slots includes an engagement surface that ramps axially about said instrument head.

6. An instrument as recited in claim 5, wherein said pin of said actuator knob is provided in one of said annular securing slots which does not include a ramped engagement surface after said tip element is rotatably secured to said instrument head.

7. An instrument as recited in claim 1, including a plurality of otoscopic speculum tip elements, each of said speculum tip elements including an axisymmetric body having a plurality of external engagement features.

* * * * *